United States Patent
Leary et al.

(10) Patent No.: US 7,019,845 B1
(45) Date of Patent: Mar. 28, 2006

(54) MEASURING ELASTIC MODULI OF DIELECTRIC THIN FILMS USING AN OPTICAL METROLOGY SYSTEM

(75) Inventors: Sean P. Leary, Lancaster, PA (US); Guray Tas, Flanders, NJ (US); Christopher J. Morath, Morristown, NJ (US); Michael Kotelyanskii, Chatham, NJ (US); Tong Zheng, Rockaway, NJ (US); Guenadiy Lazarov, Landing, NJ (US); Andre D. Miller, Portland, OR (US); George A. Antonelli, Portland, OR (US); Jamie I. Ludke, Portland, OR (US)

(73) Assignee: Rudolph Technologies, Inc., Flanders, NJ (US)

( * ) Notice: Subject to any disclaimer, the term of this patent is extended or adjusted under 35 U.S.C. 154(b) by 35 days.

(21) Appl. No.: 10/960,351

(22) Filed: Oct. 6, 2004

(51) Int. Cl.
*G01B 9/02* (2006.01)
*G01B 11/28* (2006.01)

(52) U.S. Cl. ............... 356/504; 356/502; 356/630

(58) Field of Classification Search ............... 356/450, 356/451, 502–504, 601, 630, 432
See application file for complete search history.

(56) References Cited

U.S. PATENT DOCUMENTS

| | | | |
|---|---|---|---|
| 4,710,030 A | 12/1987 | Tauc et al. | 356/432 |
| 5,706,094 A | 1/1998 | Maris | 356/432 |

(Continued)

FOREIGN PATENT DOCUMENTS

JP    405346309 A    * 12/1993

OTHER PUBLICATIONS

Femtosecond pump-probe nondestructive examination of materials, Norris et al, Review of Scientific Instruments, Jan. 2003, pp400-406.*

(Continued)

*Primary Examiner*—Gregory J. Toatley, Jr.
*Assistant Examiner*—Patrick Connolly
(74) *Attorney, Agent, or Firm*—Harrington & Smith, LLP

(57) ABSTRACT

An optical metrology system is provided with a data analysis method to determine the elastic moduli of optically transparent dielectric films such as silicon dioxide, other carbon doped oxides over metal or semiconductor substrates. An index of refraction is measured by an ellipsometer and a wavelength of a laser beam is measured using a laser spectrometer. The angle of refraction is determined by directing a light pulse focused onto a wafer surface, measuring a first set of $x_1$, $y_1$, and $z_1$ coordinates, moving the wafer in the z direction, directing the light pulse onto the wafer surface and measuring a second set of $x_2$, $y_2$ and $z_2$ coordinates, using the coordinates to calculate an angle of incidence, calculating an angle of refraction from the calculated angle of incidence, obtaining a sound velocity v, from the calculated angle of refraction and using the determined sound velocity v, to calculate a bulk modulus. Hardware calibration and adjustments for the optical metrology system are also provided in order to minimize the variation of the results from tool to tool down to about 0.5% or below.

36 Claims, 4 Drawing Sheets

U.S. PATENT DOCUMENTS

| | | | |
|---|---|---|---|
| 5,748,318 A | 5/1998 | Maris et al. | 356/630 |
| 5,844,684 A | 12/1998 | Maris et al. | 356/432 |
| 5,864,393 A | 1/1999 | Maris | 356/28 |
| 6,008,906 A | 12/1999 | Maris | 356/432 |
| 6,016,202 A * | 1/2000 | Fuchs et al. | 356/502 |
| 6,025,918 A | 2/2000 | Maris | 356/388 |
| 6,038,026 A | 3/2000 | Maris | 356/514 |
| 6,504,618 B1 * | 1/2003 | Morath et al. | 356/630 |
| 6,621,582 B1 | 9/2003 | Wolf | 356/601 |

OTHER PUBLICATIONS

"A High-Resolution Technique for Multidimensional NMR Spectroscopy", Ye Li, et al., IEEE Transactions On Biomedical Engineering, vol. 45, No. 1, Jan. 1998, pp. 78-86.

* cited by examiner

MEASURING ELASTIC MODULI OF DIELECTRIC THIN FILMS USING AN OPTICAL METROLOGY SYSTEM

TECHNICAL FIELD

This invention relates generally to optical metrology methods and apparatus and, more specifically, relates to measuring elastic moduli of dielectric thin films.

BACKGROUND

The increasing sophistication of semiconductor technology has resulted in a significant shift away from aluminum as the dominant metal in multi-level metallization processes. As semiconductor chip manufacturing has moved from AlCu/SiO2 based interconnect technology to Cu/Low k ILD (low dielectric constant interlayer dielectrics) technology, several integration issues such as delamination, peeling, and cracking have become apparent. Accordingly, these issues have evidenced a need for accurate measurement and control of the mechanical strength of the dielectric layers.

Nano-indentation and bending tests have been the commonly used methods to determine the elastic moduli of both opaque and transparent materials. With nano-indentation, a load is applied to an indenter to force it into a material. As the indenter is forced into the material, the amount that the indenter is displaced into the material is measured. Concurrently with the measurement of the indenter displacement, the load applied to the indenter is measured. However, when forcing an indenter into a thin film, not only will the thin film deform, but the substrate will deform as well. Bending tests apply strain to measure failure characteristics of a material.

When applied to thin films, these methods fail to accurately describe behavior as the scale of thin films is reduced to micron and sub-micron dimensions. Because both nano-indentation and bending tests are destructive, are contact based in nature, and have large errors and very low throughput, they are not suitable for semiconductor process control. Another disadvantage of these methods is that they require larger test areas than the area that the typical process design rules allow.

As can be appreciated, a non-destructive, non-contact, small spot, high throughput and high accuracy method is needed that is compatible with semiconductor production throughput requirements, and for accurate measurement and control of the elastic moduli of the dielectric films used in the semiconductor industry.

SUMMARY OF THE PREFERRED EMBODIMENTS

The foregoing and other problems are overcome, and other advantages are realized, in accordance with the presently preferred embodiments of these teachings.

A method is provided which uses an optical metrology system to determine the elastic moduli of optically transparent dielectric films such as silicon dioxide, Black Diamond™, Coral™, other carbon doped oxides over metal or semiconductor substrates. A light pulse (pump) focused onto the wafer surface generates a sound wave traveling through the dielectric film. In one aspect, a second light pulse (probe) from the same or a different laser focused onto the same spot measures the changes in the optical reflectivity of the wafer. The reflected probe beam includes two components, one from the dielectric/substrate interface and one from the propagating sound wave in the dielectric film. The period of the interference of these two components of the reflected probe beam is used to determine the elastic moduli of the dielectric layer. In another aspect, the same result is obtained by directing the second light pulse onto a different spot along the surface, where there the optical reflectance at the first and second spots differ, such as where there is a different dielectric film at the two spots in a reference sample.

The data analysis method enables the determination of the period from the measured signal with, for example, +/−0.5% accuracy. The invention further provides hardware calibration and adjustments to the optical metrology system in order to minimize the variation of the results from tool to tool down to about 0.5% or below.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein.

DETAILED DESCRIPTION OF THE PREFERRED EMBODIMENTS

This invention provides a method to measure the elastic moduli of optically transparent dielectric films on opaque substrates using an optical metrology system. One suitable and non-limiting type of optical metrology system is known as the MetaPULSE™ system, which is available from the assignee of this patent application. Reference can also be made to, as example, U.S. Pat. No. 6,621,582, "Optical metrology system and method employing laser-server supplying laser energy to distributed slave metrology heads," and U.S. Pat. No. 5,748,318, "Optical stress generator and detector."

Figure 1:
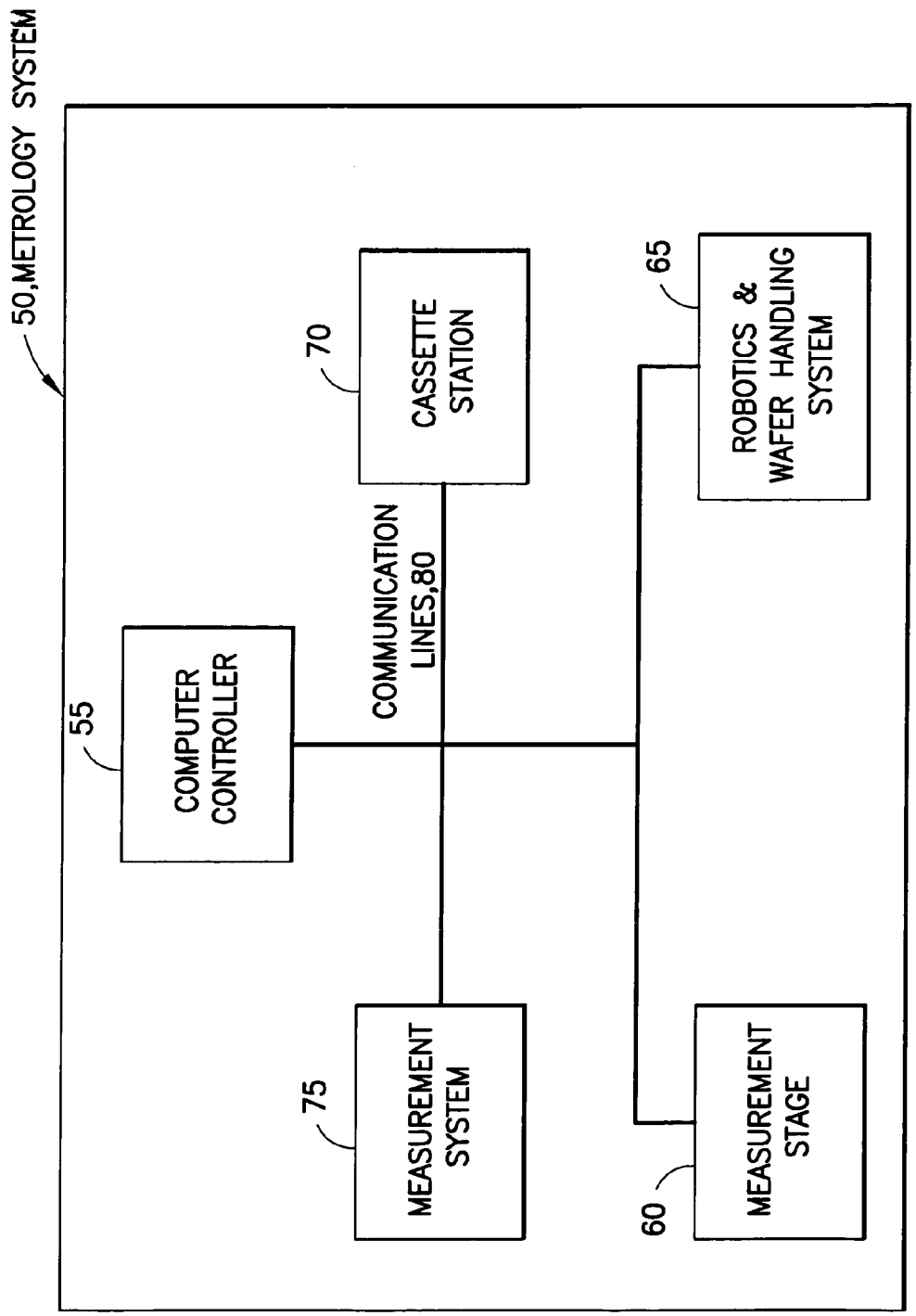
FIG. 1 is a block diagram of an optical metrology system.

By way of introduction, and referring to FIG. 1, there is shown a metrology system 50 that includes measurement stage 60, robotics and wafer handling system 65, measurement system 75, cassette station 70, computer controller 55, and communication lines 80. Computer controller (controller) 55 may be a commonly available personal computer system and is electrically connected to measurement system 75, measurement stage 60, robotics and wafer handling system 65, and cassette station 70 via communication lines 80. Controller 55 further includes software embodied in a computer-readable medium (not shown) capable of carrying out the steps of the present invention.

In operation, controller 55 sends an instruction to the robotics and wafer handling system 65 to extract a wafer from cassette station 70, and to position the wafer on the measurement stage 60. The controller 55 then issues commands to the measurement stage 60 to position the wafer relative to the measurement system so that measurements can be made at a predetermined location. The controller 55 then issues commands to the measurement system 75 to make a measurement and display the results of the measurement. Once the measurement is complete, the controller 55 issues instructions to the robotics and wafer handling system 65 to return the wafer to the cassette station 70.

The measurement stage 60 includes a test surface upon which the wafer is placed for measurements, and translation stages to provide wafer manipulation in three degrees of freedom.

Figure 2:
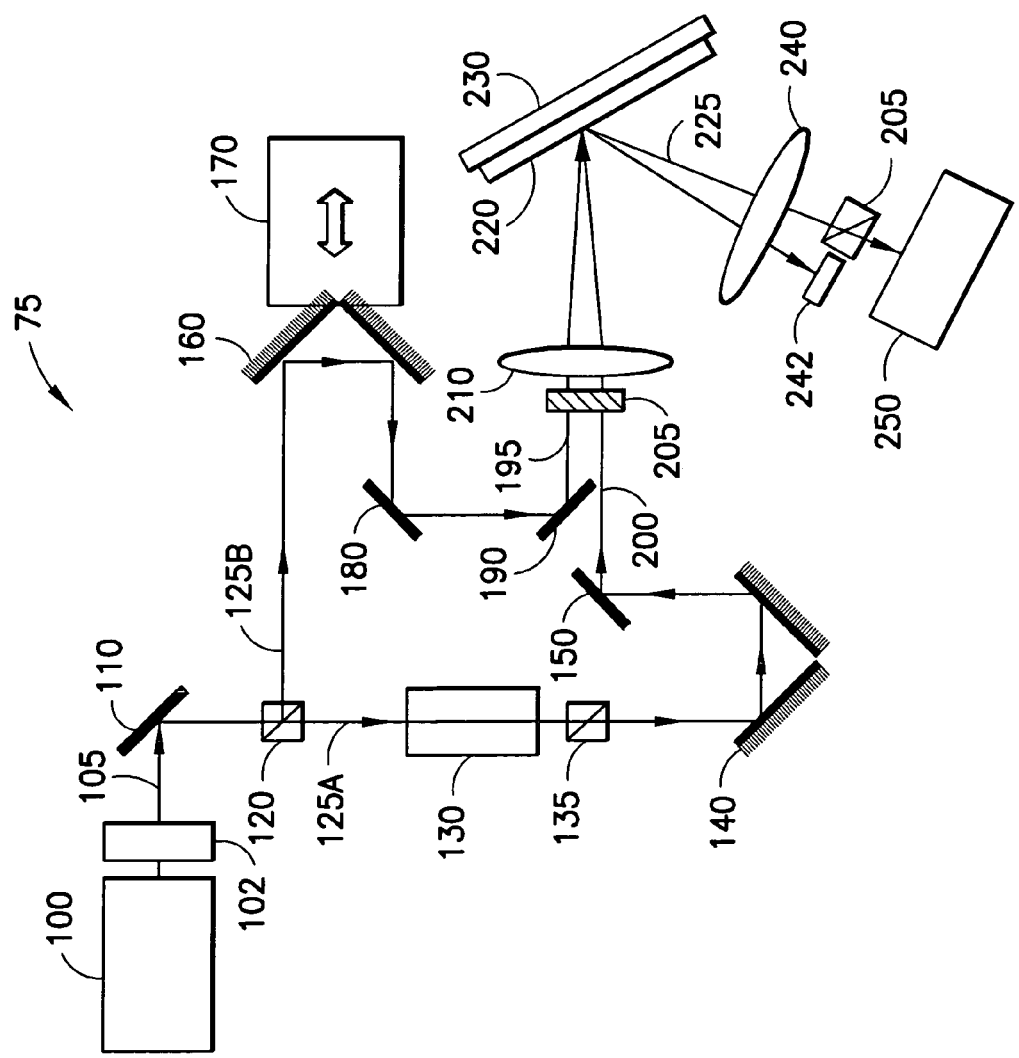
FIG. 2 is a block diagram of a photoacoustic film thickness measurement system wherein the optical paths are illustrated.

FIG. 2 is a schematic diagram of a photoacoustic measurement system 75 that includes, as arranged in FIG. 2, a pulsed light source 100, a sample stage 220, a stage/vacuum chuck 230, a first probe steering mirror 180, a pump beam steering mirror 150, a first steering mirror 110, a pump-probe beamsplitter 120, a polarizer 135, and an electro-optic modulator (EOM) 130. Additionally, photoacoustic system 75 includes a probe retroreflector 160, a delay scanning stage 170, a dither EOM 205, a beam dump 242, and a detector 250. Furthermore, photoacoustic measurement system 75 includes a linear pump-discriminating polarizer 245, a harmonic generator wavelength selector (wavelength selector) 102, a projecting lens 210, a collimating lens 240, a pump retroreflector 140, and a second probe steering mirror 190.

Pulsed light source 100 may be a titanium-sapphire laser operating at 80 MHz and emitting light at 800 nm. The laser can also be alternatively configured with a frequency doubling birefringent crystal to emit laser beam 105 at 400 nm. Other types of lasers operating with different wavelengths and different frequencies can be used as well.

In operation, pulsed light source 100 emits laser beam 105 that is re-directed by first steering mirror 110. Pump probe beamsplitter 120 splits incident laser-beam pulse (preferably of picosecond or shorter duration) into pump beam 125A and probe beam 125B. Electro-optic modulator (EOM) 130 rotates pump beam 125A polarization between horizontal and vertical at a frequency of, for example, 10 kHz to 10 MHz. Polarizer 135 converts pump beam 125A polarization rotation into an amplitude-modulated pump beam 200. Pump retroreflector 140 and pump beam steering mirror 150 deflect modulated pump beam 200 onto dither EOM 205.

A probe beam 125B is transmitted to probe retroreflector 160 where delay scanning stage 170 is used to modify the length of the beam path of probe beam 125B relative to the length of modulated pump beam 200, thus forming time delayed probe beam 195. Delayed probe beam 195 and modulated pump beam 200 propagate through dither EOM 205 and then through projecting lens 210 and finally onto sample 220. Stage/vacuum chuck 230 acts as a positioning unit for the sample wafer and is preferably a multiple-degree of freedom stage that is adjustable in height (z-axis), position (x and y-axes), and tilt (T), and allows motor controlled positioning of a portion of the sample relative to the modulated pump beam 200 and delayed probe beam 195. Alternatively or additionally, the stage may have rotational freedom of movement. The z-axis is used to translate the sample vertically into the focus region of the pump and probe beams, the x and y-axes translate the sample parallel to the focal plane, and the tilt axes adjust the orientation of the sample 220 to establish a desired angle of incidence for the probe beam.

Modulated pump beam 200 and delayed probe beam 195 propagate through collimating lens 240 where the modulated pump beam 200 is gathered by beam dump 242. Pump-discriminating polarizer 245 isolates reflected probe beam 225 from the modulated pump beam 200. Detector 250 converts reflected probe beam 225 into a signal versus delay stage 170 position. This signal is demodulated and sent to controller 55 (shown in FIG. 1) for analysis (e.g. to determine film thickness).

Presently preferred techniques for performing the analysis to determine film thickness, as well as to determine other film characteristics, can be found in the following U.S. Pat. No. 4,710,030, "Optical Generator and Detector of Stress Pulses"; U.S. Pat. No. 5,706,094, "Ultrafast Optical Technique for the Characterization of Altered Materials"; U.S. Pat. No. 5,748,318, "Optical Stress Generator and Detector"; U.S. Pat. No. 5,844,684, "Optical Method for Determining the Mechanical Properties of a Material"; U.S. Pat. No. 5,864,393, "Optical Method for the Determination of Stress in Thin Films"; U.S. Pat. No. 6,008,906, "Optical Method for the Characterization of the Electrical Properties of Semiconductors and Insulating Films"; U.S. Pat. No. 6,025,918, "Apparatus and Method for Measurement of the Mechanical Properties and Electromigration of Thin Films" and U.S. Pat. No. 6,038,026, "Apparatus and Method for the Determination of Grain Size in Thin Films", all of which are incorporated by reference herein in their entireties.

Figure 3B:
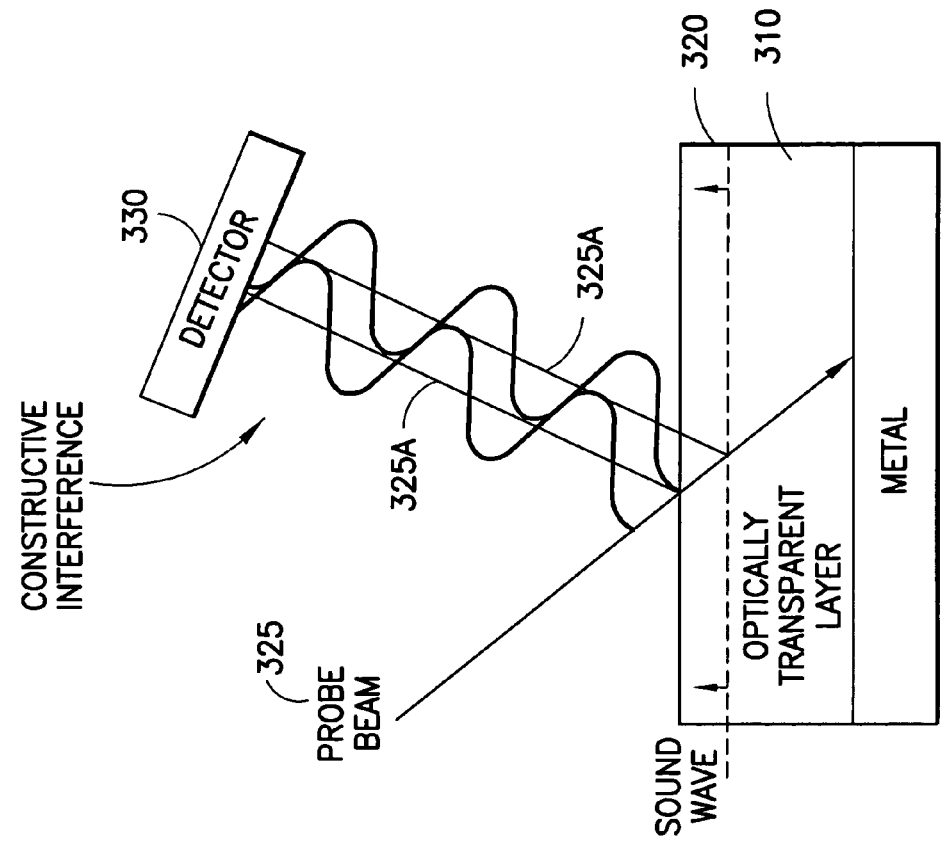
FIG. 3 illustrates a pump pulse as it passes through the transparent interlayer dielectric according to the present invention.
Figure 3A:
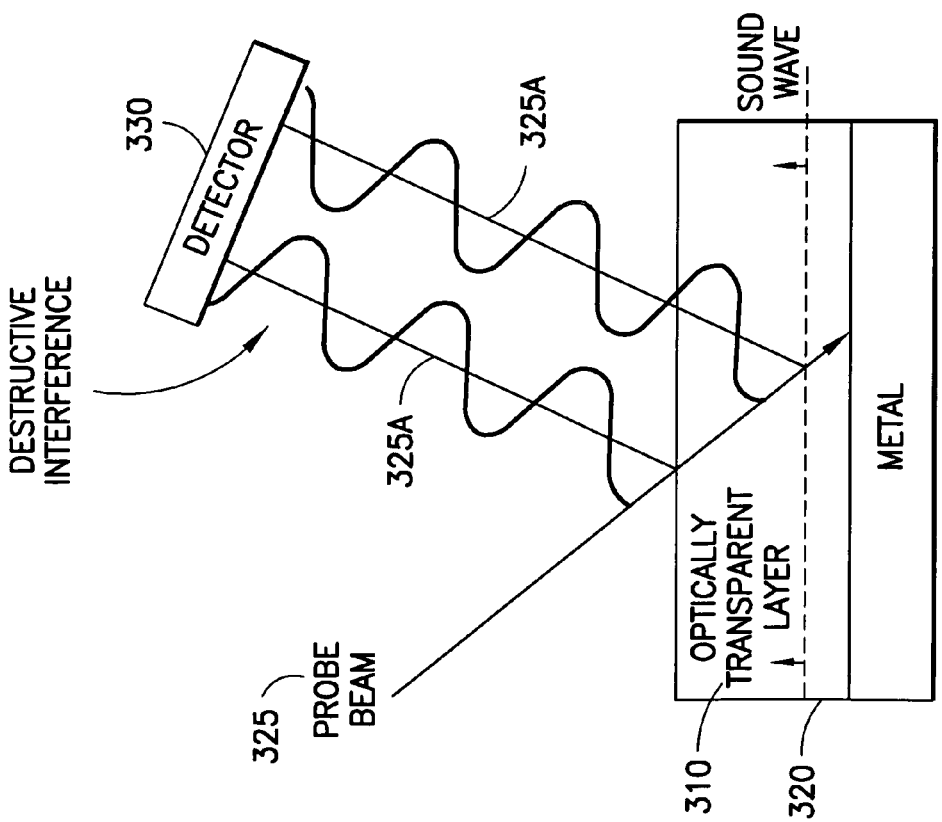

Referring now to FIGS. 3A and 3B collectively referred to as FIG. 3, the optical metrology system 50 is configured to measure the elastic moduli of the optically transparent dielectric films on opaque substrates. A light pulse (pump) passing through a dielectric film 310 and focused onto a 5×7 micron$^2$ spot on the substrate surface generates a sound wave 320, illustrated as a dashed line, traveling through the dielectric film 310. A second light pulse (probe) 325 from the same or a different laser focused onto the same spot, measures the optical reflectivity of the dielectric film 310 modified by the sound wave 320. The reflected probe beam 325A has two components, one from the dielectric/substrate interface and one from the sound wave 320 as it travels in the dielectric layer 310. As the sound travels in the dielectric layer 310, it causes small local changes in the optical properties which reflect the probe beam 325. These two components of the probe beam interfere at a detector 330 resulting in a signal oscillating with a fixed period. The period of the oscillations depends on the wavelength of the probe beam 325, the incident angle of the probe beam 325, the sound velocity in the dielectric film 310, and the index of refraction of the dielectric film 310. FIG. 3A shows the case where the reflected probe beam 325 destructively interferes with itself, and FIG. 3B shows the case where the reflected probe beam 325A constructively interferes.

The period of the oscillations can be used to determine the sound velocity v, in the dielectric layer 310 using $$v = \lambda/2n\tau \cos\theta \qquad (\text{Eq. 1})$$

where n is the index of refraction of the dielectric layer 310; $\tau$ is the period of the interference oscillations; $\lambda$ is the wavelength of the probe beam 325; and $\theta$ is the angle of refraction.

The elastic stiffness of the dielectric film 310 is described by $c_{1111} = \rho v^2$. Young's modulus (Y) of the dielectric film can then be calculated by:

$$Y = 1/s_{1111} = \rho v^2 (1 - 2v)(1 + v)/(1 - v). \qquad (\text{Eq. 2})$$

Similarly the Bulk Modulus of the dielectric film 310 can be calculated using:

$$B = \rho v^2 (1+v)/3(1-v), \quad \text{(Eq. 3)}$$

where $\rho$ and $v$ are the density and Poisson's ratio of the dielectric film 310.

Figure 4:
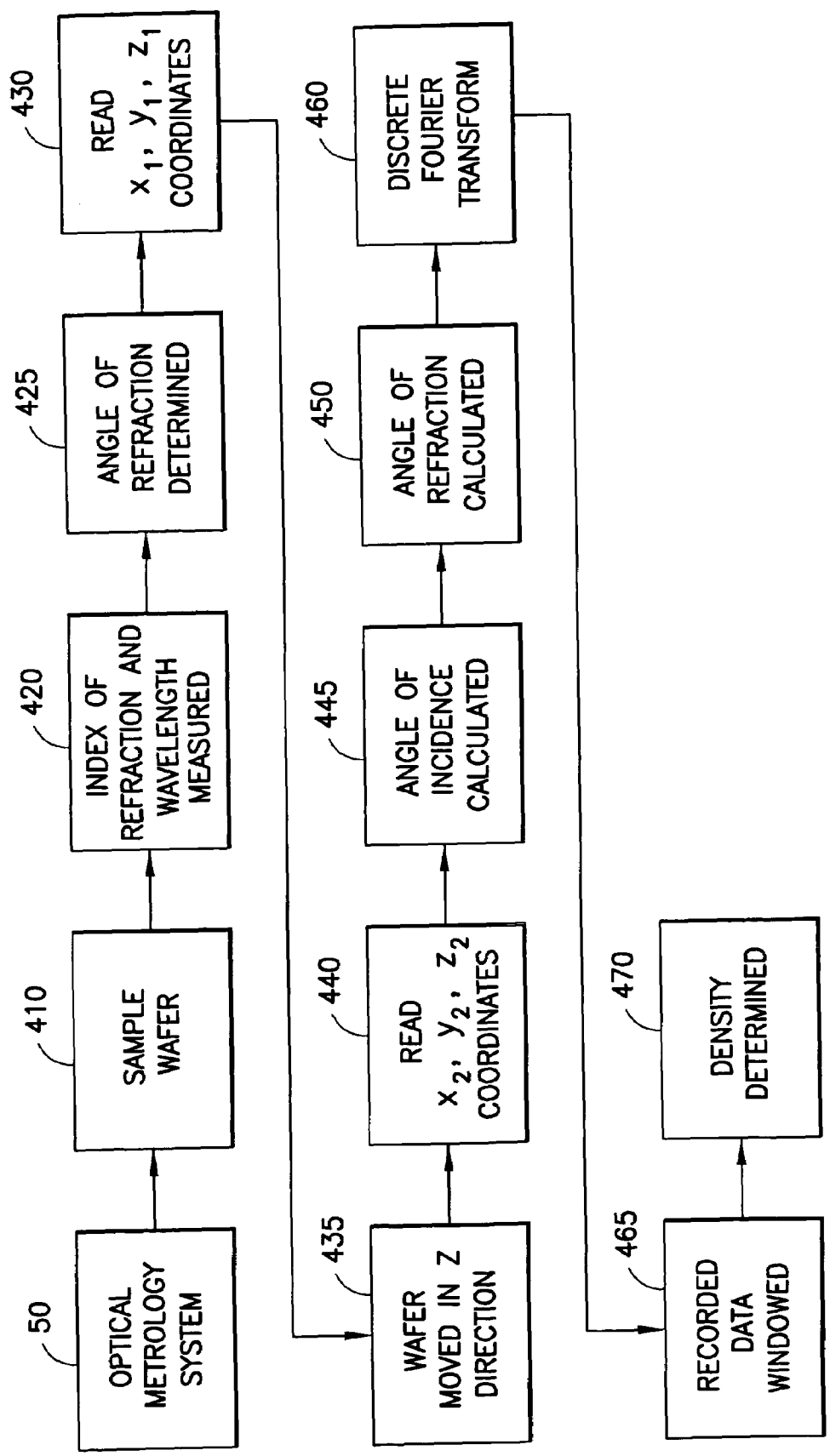
FIG. 4 is a flow chart that illustrates the method of calibrating the metrology system according to the present invention.

Additionally, in order to determine the elastic moduli with the accuracy and repeatability required for semiconductor process monitoring, while minimizing the variation of the results from tool to tool, a method, as illustrated in FIG. 4, is provided with several hardware adjustments for determining the value of each parameter in Eq. 1.

The index of refraction, if not known a priori, may be measured by an ellipsometer, and the wavelength of the laser beam may be measured using a laser spectrometer 420 that is integrated inside the metrology system. Wavelength measurement accuracy of better than 0.1% is attainable with commercially available compact spectrometers (e.g. Ocean Optics model S2000), and it can be seen by Eq. 1 that this accuracy is sufficient to achieve 0.5% accuracy in the modulus measurement. The angle of refraction is determined by the following method.

A $SiO_2$ pattern wafer or a reference chip (cut from a $SiO_2$ pattern wafer) with areas of two different films with contrasting optical reflectance, for example native and 1000 Angstrom $SiO_2$, can be also be used for the measurement. The probe beam scans across the edges in both the x and y direction of a measurement area with the 1000 Angstrom $SiO_2$ residing in an area with native oxide (or vice versa). Since the reflectivity of the laser is different between these two films, two curves are generated from the scans, one for the scan in the x direction and one for the scan in the y direction. By fitting each curve to a complementary error function (based on the assumption that the intensity of the laser beam has a Gaussian distribution), the spot location and size in both the x and y directions can be obtained. The spot locations (x, y) are detected by this method at different positions in the z direction. The angle of incidence (AOI) at block 445 is calculated by:

$$AOI = \text{ArcTan}([(x_2 - x_1)^2 + (y_2 - y_1)^2]^{1/2} / (z_2 - z_1)).$$

To increase the accuracy in the AOI measurements, one can measure the laser beam location (x, y) for successive six or seven positions in the z direction, and use linear data modeling to reduce noise. With one time setup, these measurements of angle and wavelength can be performed automatically without any user intervention.

In a presently preferred embodiment a near normal incidence angle may be used. The presently preferred optical metrology system shown at block 50 operates at a probe angle of incidence of about 40 degrees with respect to normal. As the probe incidence angle becomes smaller (more normal to the film), the angle-dependent term in Eq. 1 becomes less sensitive to uncertainty in the angle, and measurement matching between systems improves.

A discrete Fourier transform (DFT) 460 preferably is used to analyze the frequency content of the signal to obtain the period. The DFT 460 is well suited to find the frequency of sine waves in high frequency noise. However the DFT 460 is circular in nature and if the beginning and ends do not match, an artifact called 'spectral leakage' (smearing of the spectrum) will occur. Another artifact is known as scalloping or 'picket fence' effect. This results when the actual frequency of the wave does not correspond with the frequency resolution of the DFT 460. The frequency resolution of a DFT 460 is the ratio of the sampling frequency $f_s$ to the number of digitized samples N. Because the signal from the interlayer dielectric is not stationary (i.e. it changes with time), due to sound reflections at interfaces and acoustic damping, it is difficult to arbitrarily increase N by taking longer measurements. However, sinc or frequency preserving interpolation in the frequency domain can be accomplished in the frequency domain by simply zero-padding in the time domain.

To combat the artifacts associated with the DFT 460, the following algorithm is preferred for use. Recorded data is windowed 465 using a rectangular or 'boxcar' function to ensure an integral number of wavelengths present. The DFT 460 is performed. An ideal filter is applied that has a center frequency equal to the frequency at which the maximum amplitude occurs and narrow bandwidth that is a function of the center frequency. Sinc-interpolation in the frequency domain is performed on the resulting spectrum and a peak refinement algorithm is used to find a high precision value of the frequency of oscillation.

In addition to the oscillatory component coming from the interference of the reflected probe beam components that carry information about the sound velocity, the signal, measured by the optical metrology system contains "background" contribution due to the dissipation of the heat energy delivered by the pump pulse. This component is slowly decaying with time. This component additionally contributes to the signal being non-stationary, and decreases the accuracy obtained using the DFT 460 method. In addition, this background component depends on the fine details of the optical alignment and contributes to the tool-to-tool variability. Thermal background can be subtracted by fitting an exponential or a polynomial function to the signal, and subtracting it.

To obtain fine frequency resolution and sensitivity of the measurement, the sinc-interpolation is done on the padded dataset, which may contain several times more data points. The sinc-interpolation may become time-consuming due to the increased dataset.

A faster algorithm comprising the following can be used. The thermal background is subtracted by fitting a low order polynomial function to the raw data. The resulting signal is de-noised by using Ideal frequency filtering. Ideal frequency filtering involves applying the DFT transform 460, finding the maximal intensity frequency within the pre-specified range, removing any component outside the narrow band surrounding the maximal intensity component, and calculating the inverse DFT to obtain the de-noised data in the time domain.

As this signal consists of a single frequency oscillation, the signals' period can be determined by locating the times of its maxima and minima using a peak refinement algorithm. These times can be obtained with improved resolution over the resolution obtained by time sampling of the signal.

Separations between the peaks can be averaged over the pairs of peaks, separated by at least $k_{min}$ counts, to obtain the oscillation period T by using the following formula for a set of M extrema times $\{e_i\}$, sorted by the peak time in ascending order:

$$T = \frac{1}{N_p} \sum_{k=k_{\min}}^{k=k_{\max}} \sum_{i=1,M-k} \frac{e_{i+k} - e_i}{k}.$$

It is important to exclude the close peaks as much as possible, as they contribute more variability to the answer.

Alternatively, by linear fitting peak times vs. peak number, the slope and the intercept may be obtained. The slope equals one half of the oscillation period.

In the situation where the ILD film is thinner, and only a few, or no oscillation periods can be observed before the first sound reflection from the bottom of the film, the above methodology may not be adequate. In this situation MUSIC or DMUSIC algorithms can be used, or alternatively some non-linear fitting of the signal with the single frequency sinusoid, optimizing its amplitude, phase and frequency to obtain the best fit to the data. The goal function of such optimization can be either the usual Fit Error defined as a sum of the squares of the differences between the measured and fitted signal, or the cross-correlation of the fitted and measured signals.

Density can be determined 470 by measuring the amplitude change between the oscillations incident and reflected at the dielectric/Si interface by the following:

$$R = B/A = (Z_{substrate} - Z_{dielectric})/(Z_{substrate} + Z_{dielectric}) \quad \text{(Eq. 4)}$$

$$\rho = Z/v, \quad \text{(Eq. 5)}$$

where R is the reflection coefficient, A is the incident wave amplitude, B is the reflected wave amplitude, and Z is the characteristic acoustic impedance. It is assumed that the characteristic acoustic impedance is known for the Si substrate. For the Young's modulus or the Bulk modulus calculations, the published value of the Poisson's ratio can be used.

It is noted that another technique to address the problem solved by the teachings of this invention includes a narrow-bandwidth/long pulse system. The 100 fsec laser pulses generated by titanium sapphire lasers typically have bandwidths on the order of 10 nm at 800 nm and doubled pulses have bandwidths around 3 nm. Longer pulse widths, around 1 psec, may be used to practice this technique and these pulses have significantly smaller bandwidths (<1 nm). The smaller bandwidth improves the accuracy of the technique via Eq. 1 by limiting the range of wavelengths.

Another alternative includes the use of a derivative mode modulus measurement system, as the oscillatory nature of the measurement signals lends these measurements to a derivative type of measurement (see, for example, U.S. Pat. No. 5,748,318). The result is an improved signal to noise ratio, leading to improved repeatability and shorter measurement time (higher throughput).

A further alternative includes the use of tilt correction. The wafer tilt relative to the optics head contributes to uncertainty in the angle as calculated in Eq. 1. Such tilts can be different depending on measurement location across the sample due to sample, chuck, or stage non-uniformities. A tilt measurement may be performed at each site to correct for these effects, for example using a standard laser diode and position sensitive detector.

Additionally, one or more optimized "check samples" (for example $SiO_2$/Si, bare Si, and SiN/Si) with known acoustic and optical properties may be used to calibrate and/or monitor multiple optical metrology systems for improved repeatability and/or matching between systems. Such samples may be periodically loaded into the tool or included inside the tool and periodically monitored.

Another alternative includes the use of a multiple angle probe beam system. Measuring the sample at multiple known probe angles allows for an independent calculation of refractive index n in Eq. 1. This allows the system to uniquely discriminate between process variations that may impact sound velocity from those that may impact refractive index.

A further alternative includes matched spot size and pump/probe beam intensities. Previous work suggests that most film measurement results have a small empirical dependence on pump and probe spot sizes and powers. Likewise, some degree of control of these system parameters may be preferred for modulus measurement matching. Additionally, reducing uncertainty in the incident probe angle with an extremely flat chuck (<0.01 deg) leads to improved tool matching through Eqs. 1 and 2.

Film temperature compensation is another alternative. According to the experimental literature on temperature dependence of sound velocity, many films have temperature coefficients on the order of $10^{-4}$ 1/C. Therefore, to the extent that the film temperature is not similar between tools a difference in the measured sound velocity is expected. Temperature differences may be due to ambient temperature or temperature rise in the film as a result of the absorption of the laser pulses. A calibration table may be created to match tools for each material based upon the film's velocity and refractive index temperature coefficients, an accurate measurement of ambient temperature, and a calculation of film temperature rise on the basis of the measured quantities: pump and probe laser powers, spot sizes, and film reflectance.

Further, although described in terms of preferred embodiments, it should be realized that a number of modifications of the teachings of this invention may occur to one skilled in the art and will still fall within the scope of this invention. By example, the method is not limited to dielectric blanket films; it can also be applied to measure an effective value for the elastic moduli of metal/dielectric pattern structures such as in Cu/ILD damascene interconnects.

Thus, while described above in the context of presently preferred embodiments, it should be appreciated that these embodiments are not to be construed in a limiting sense upon the practice of this invention.

What is claimed is:

1. A method of optical metrology, comprising:
    laterally scanning a reference sample to induce a reflection off of the reference sample;
    locating a first set of reflected $x_1$, $y_1$ coordinates;
    moving the reference sample in a z direction;
    laterally scanning the reference sample to locate a second set of reflected $x_2$, $y_2$ coordinates; and
    calculating an angle of incidence from the located first and second sets of coordinates.

2. A method as in claim 1, further comprising calculating an angle of refraction using the calculated angle of incidence.

3. A method as in claim 2, further comprising determining a sound velocity v using the calculated angle of refraction in at least a portion of the reference sample and calculating the modulus of elasticity of at least the portion of the reference sample using the determined sound velocity v.

4. A method of optical metrology, comprising:
directing a first light pulse to a surface of a sample;
determining a first set of $x_1$, $y_1$, $z_1$ coordinates using a reflected portion of the first light pulse;
moving the sample in the z direction;
directing a second light pulse onto the surface of the sample;
determining a second set of $x_2$, $y_2$, $z_2$ coordinates using a reflected portion of the second light pulse;
calculating an angle of incidence from the first and second sets of coordinates;
calculating an angle of refraction using the calculated angle of incidence;
using the calculated angle of refraction to determine a sound velocity v in at least a portion of the sample surface; and
using the determined sound velocity v, to determine a modulus of elasticity of the portion of the sample surface.

5. A method as in claim 4, wherein the angle of refraction is calculated from the angle of incidence using Snell's law.

6. A method as in claim 4, wherein the angle of incidence is calculated using $$AOI = \text{ArcTan}([(x_2 - x_1)^2 + (y_2 - y_1)^2]^{1/2} / (z_2 - z_1)).$$

7. A method as in claim 4, wherein the sample surface comprises at least two different films.

8. A method as in claim 7, wherein the optical reflectivity is different between the at least two different films.

9. A method as in claim 7, wherein the light pulse scans across edges of the at least two different films in the x direction and the y direction generating an x direction curve and a y direction curve at different positions in the z direction to determine the angle of incidence.

10. A method as in claim 4, wherein the sample comprises a semiconductor wafer having at least one dielectric film disposed on the surface.

11. A method as in claim 10, wherein the dielectric film comprises $SiO_2$.

12. A method as in claim 10, wherein the dielectric film comprises polymer.

13. A method as in claim 10, wherein the dielectric film comprises carbon doped oxide.

14. A method of data analysis of an optical metrology system comprising:
determining an index of refraction of a sample;
determining a wavelength of a laser beam;
determining an angle of refraction of the sample by marking a surface of a first portion of the sample with a first light pulse, said first portion having a first reflectivity;
reading a first set of ($x_1$, $y_1$, $z_1$) coordinates from the system using a reflected portion of the first light pulse;
marking a surface of a second portion of the sample with a second light pulse, said second portion having a second reflectivity;
reading a second set of coordinates ($x_2$, $y_2$, $z_2$) from the system using a reflected portion of the second light pulse;
calculating the angle of incidence from the first and second set of coordinates;
calculating the angle of refraction using the calculated angle of incidence;
using the calculated angle of refraction to determine a sound velocity v, in at least a portion of the sample surface; and
using the determined sound velocity to determine a modulus of elasticity of the portion of the sample surface.

15. A method as in claim 14, wherein the angle of incidence is calculated using $$AOI = \text{ArcTan}([(x_2 - x_1)^2 + (y_2 - y_1)^2]^{1/2} / (z_2 - z_1)).$$

16. A method as in claim 14, wherein a plurality of marks are obtained and averaged to increase the accuracy of the angle of incidence measurement.

17. A method as in claim 14, wherein an oscillating signal is used to determine a sound velocity v, in a film layer using $v = \lambda/2n\tau\cos\theta$, where n is the index of refraction of the film layer, $\tau$ is a period of an interference oscillation, $\lambda$ is the wavelength of the laser beam, and $\theta$ is the angle of refraction.

18. A method as in claim 14, wherein a discrete Fourier transform algorithm is used to analyze a frequency content of a signal to obtain a period, the algorithm comprising windowing recorded data using a rectangular function to ensure an integral number of wavelengths present, performing the discrete Fourier transform, applying an ideal filter with a center frequency equal to a frequency at which the maximum amplitude occurs, sinc interpolation in the frequency domain performed on the resulting spectrum and a peak refinement algorithm to find a precision value of a frequency of oscillation.

19. A method as in claim 16, wherein a density is determined by measuring an amplitude variation between the oscillation incident and reflected at a dielectric interface using $R = B/A = (Z_{substrate} - Z_{dielectric})/(Z_{substrate} + Z_{dielectric})$ and $\rho = Z/v$ where R is a reflection coefficient, A is a incident wave amplitude, B is a reflected wave amplitude, and Z is a characteristic acoustic impedance.

20. A method as in claim 14, wherein an algorithm is used to refine a frequency resolution, the algorithm comprising subtracting a thermal background by fitting a low order polynomial function to a raw dataset, removing a noise from a resulting signal by using Ideal frequency filtering, locating the signals maxima and minima times using a peak refinement algorithm to obtain an oscillation period T of the signal, the oscillation period T obtained by using $$T = \frac{1}{N_p} \sum_{k=k_{\min}}^{k=k_{\max}} \sum_{i=1,M-k} \frac{e_{i+k} - e_i}{k}.$$

21. An optical metrology, comprising:
an optical source subsystem for laterally scanning a beam over a reference sample along x and y axes to induce a reflection off of the reference sample and for moving the reference sample relative to the beam along a z axis;
a detector for locating a first set of reflected $x_1$, $y_1$ coordinates and a second set of reflected $x_2$, $y_2$ coordinates corresponding to a first z axis location and a second z axis location, respectively; and
a processor operating under control of a stored program to calculate an angle of incidence of the beam.

22. A system as in claim 21, wherein said processor further operates to determine an angle of refraction associated with the reference sample.

23. A system as in claim 22, where the processor further determines a sound velocity v in at least a portion of the reference sample using the determined angle of refraction, and determines the modulus of elasticity in at least the portion of the reference sample using the determined sound velocity v.

24. A system as in claim 21, where said reference sample comprises a patterned reference sample.

25. An optical metrology system, comprising:
a sample stage having multiple degrees of freedom;
a detector;
at least one optical source providing a light pulse source for marking a sample with a first light pulse for determining an angle of refraction by reading a first set of $(x_1, y_1, z_1)$ coordinates from the system using a reflected portion of the first light pulse, moving the sample in the z direction and marking the sample with a second light pulse, reading a second set of $(x_2, y_2, z_2)$ coordinates from the system using a reflected portion of the second light pulse; and
a data analysis system coupled to the detector for calculating the angle of incidence from the first and second set of coordinates, calculating an angle of refraction from the calculated angle of incidence, using the calculated angle of refraction to determine a sound velocity v, and using the determined sound velocity to determine a modulus of elasticity of the sample.

26. A system as in claim 25, wherein the data analysis system uses $AOI=ArcTan([(x_2-x_1)^2+(y_2-y_1)^2]^{1/2}/(z_2-z_1))$ to calculate the angle of incidence.

27. A system as in claim 25, where the index of refraction is measured using an ellipsometer.

28. A system as in claim 25, wherein the optical source comprises a laser, and a wavelength of the laser is measured using a spectrometer.

29. An optical metrology system as in claim 25, wherein the light pulse source is used to obtain a plurality of marks which are averaged to increase the accuracy of the angle of incidence measurement.

30. An optical metrology system as in claim 25, wherein the sample comprises at least two different films.

31. A program of computer readable instructions, embodied on a computer readable medium and executable by a digital processor, for determining a quality metric in a reference sample, the actions comprising:
determining a first set of coordinates using a first induced reflection from the reference sample;
determining a second set of coordinates using a second induced reflection from the reference sample, said second induced reflection emanating from a point of the reference sample different from that of the first induced reflection; and
calculating an angle of incidence from the determined first and second sets of coordinates.

32. The program of claim 31, wherein the actions further comprise:
calculating an angle of refraction using the calculated angle of incidence;
using the calculated angle of refraction to determine a sound velocity v in at least a portion of the sample surface; and
using the determined sound velocity v, to determine a modulus of elasticity of the portion of the sample surface.

33. The program of claim 31, wherein a first laser pulse induces the first reflection, and a second laser pulse induces the second reflection.

34. The program of claim 33, wherein the first induced reflection occurs when the reference sample is in a first position relative to a laser from which the first pulse emanates, and wherein the second induced reflection occurs when the reference sample is in a second position relative to the laser.

35. The program of claim 34, wherein both the first and second pulses emanate from the laser.

36. The program of claim 31, wherein the actions further comprise:
positioning the reference sample in a first position relative to a light source prior to the first induced reflection from that light source; and positioning the reference sample in a second position relative to the light source prior to the second induced reflection.

* * * * *